United States Patent [19]
Ogle, deceased

[11] Patent Number: 4,595,262
[45] Date of Patent: Jun. 17, 1986

[54] TUNABLE BIREFRINGENT SAFETY GOGGLES FOR LASER BEAMS

[75] Inventor: Norman E. Ogle, deceased, late of Palo Alto, Calif., by Barbara Ann Ogle, administratrix

[73] Assignee: Lockheed Missiles & Space Company, Inc., Sunnyvale, Calif.

[21] Appl. No.: 643,535

[22] Filed: Aug. 23, 1984

[51] Int. Cl.⁴ .................... G02B 5/30; G02C 7/12
[52] U.S. Cl. .................... 350/404; 350/407; 351/49
[58] Field of Search .................. 2/432, 8; 351/49; 350/403, 407, 404

[56] References Cited
U.S. PATENT DOCUMENTS 3,368,652  2/1968  Klatchlto ............... 350/407
3,944,346  3/1976  Shindler ............... 350/407
4,201,450  5/1980  Trapani ............... 351/49

OTHER PUBLICATIONS

Title et al, *Tunable Birefringent Filter*, Optical Engineering, vol. 20, No. 6, 11-1981, pp. 815-823.

Primary Examiner—John K. Corbin
Assistant Examiner—B. S. Shapiro
Attorney, Agent, or Firm—John J. Morrissey

[57] ABSTRACT

A set of safety goggles (20) for adjustably attenuating the intensity of optical radiation at any selected wavelength produced by a variable-wavelength laser (e.g., a dye laser) comprises a pair of oculars, both of which can be tuned to any particular wavelength producible by the laser. Each ocular comprises a birefringent filter, which includes stationary components including a polarizer (11), a wide-field element made up of a half-wave plate (13) sandwiched between multiwave plates (12 and 14), and a quarter-wave plate (16), and rotatable components including a polarizer (18). The wide-field element causes an optical path difference between orthogonal components of a single polarization state. The quarter-wave plate (15) and the rotatable polarizer (18) in combination enable selection of any particular wavelength whose intensity is to be attenuated. Both oculars are coupled so that rotation of the polarizer (18) of one ocular through a selected angle results in simultaneous rotation of the polarizer (18) of the other ocular through the same angle.

9 Claims, 5 Drawing Figures

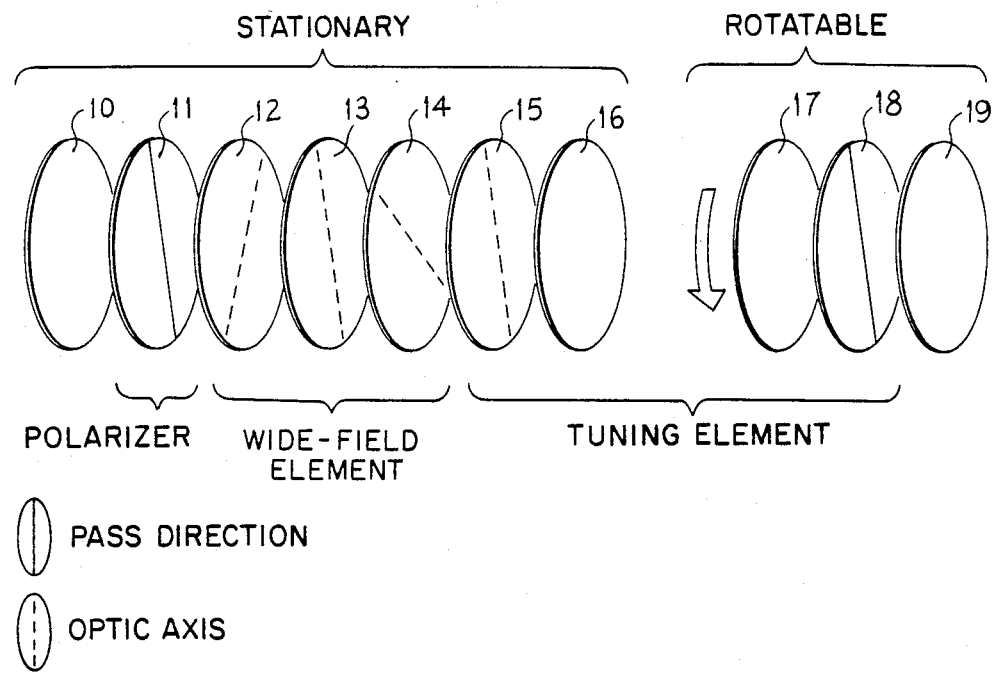
FIG_1
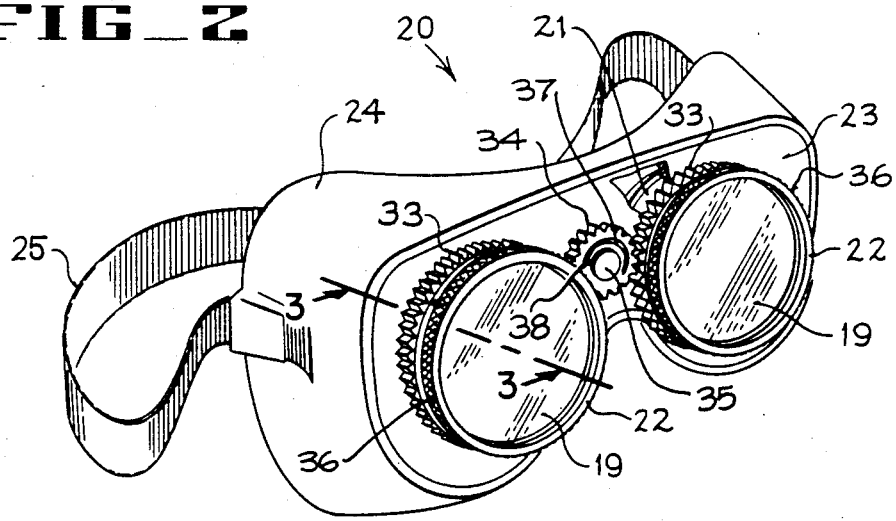
FIG_2

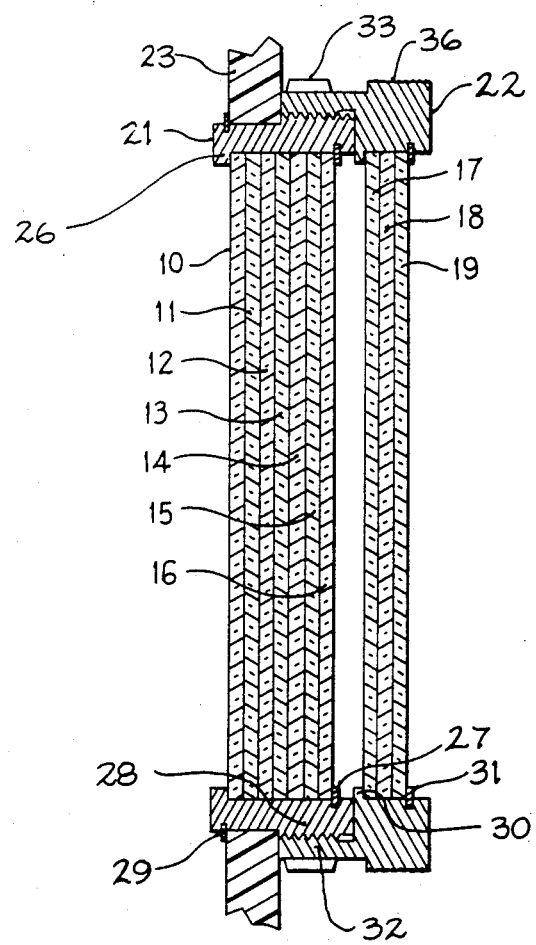
FIG_3
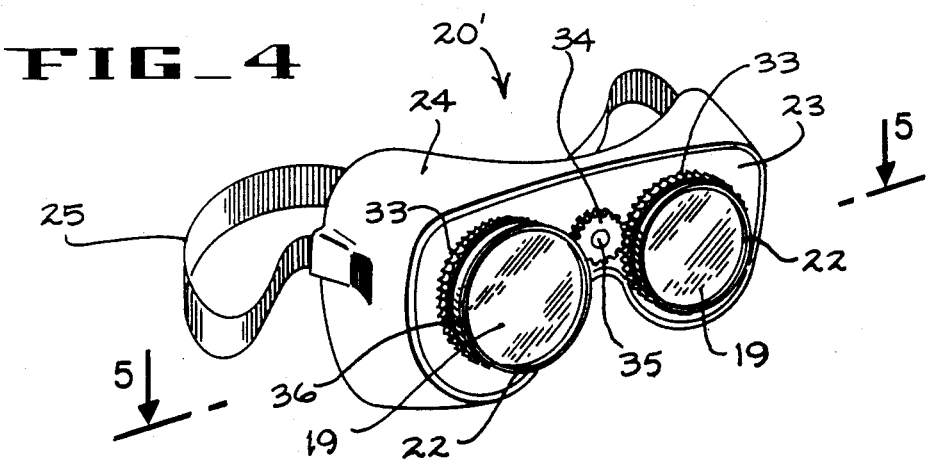
FIG_4

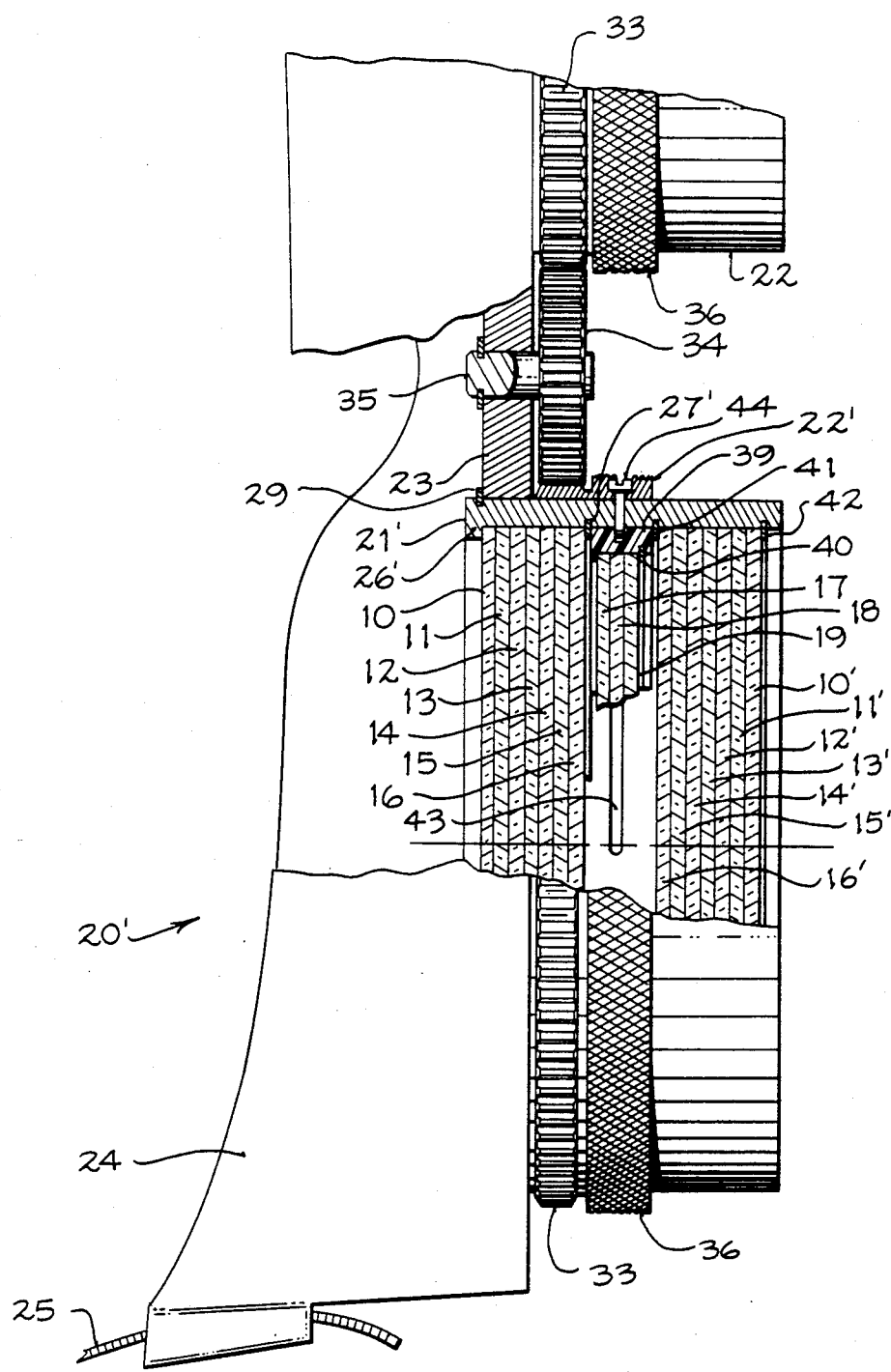
FIG_5

TUNABLE BIREFRINGENT SAFETY GOGGLES FOR LASER BEAMS

TECHNICAL FIELD

This invention pertains generally to eye-protective apparatus, and more particularly to tunable goggles for attenuating radiation in a broad spectral band produced by a variable-wavelength laser device.

BACKGROUND ART

Until recently, laser devices for commercial and experimental applications had been capable of producing beams of coherent optical radiation only at discrete wavelengths. Eye-protective goggles for use with such discrete-wavelength laser devices were correspondingly sensitive to discrete wavelengths. Thus, a researcher working with a number of different laser devices for producing beams of coherent radiation at a number of different wavelengths generally needed a corresponding number of different sets of safety goggles, i.e., a different set of goggles for each laser wavelength being produced.

Recently, variable-wavelength dye lasers (i.e., laser devices using a complex organic "dye" as the lasing element) have become commercially available for producing beams of coherent optical radiation at selectable wavelengths in a broad spectral band. Dye lasers are marketed by, e.g., Coherent Inc. of Palo Alto, Calif. and Spectra-Physics Inc. of Mountain View, Calif. However, until the present invention, there had been no tunable eye-protective gear available for use with variable-wavelength dye lasers.

Researchers working with variable-wavelength dye lasers have perceived a need for tunable eye-protective goggles capable of attenuating a selected wavelength while passing a broad band of optical radiation. Tunable birefringent filters have been used in astronomical applications for selectively passing or blocking particular wavelengths of radiation from distant sources such as solar flares. However, until the present invention, practitioners in the art relating to eye-protective gear did not recognize that tunable birefringent filter devices could be adapted for use in adjustably attenuating the intensity of radiation from variable-wavelength lasers. An article entitled "Tunable Birefringent Filters" by A. M. Title and W. J. Rosenberg, published in *Optical Engineering*, Vol. 20, No. 6, (Nov.–Dec. 1981), pp. 815–821, provides a technical description of tunable birefringent filters.

SUMMARY OF THE INVENTION

It is an object of the present invention to provide eye-protective gear for adjustably attenuating the intensity of radiation at selectable wavelengths produced by a variable-wavelength laser.

It is a more particular object of the present invention to adapt a tunable birefringent filter for use as an ocular in a set of safety goggles for adjustably attenuating the intensity of radiation at any selected wavelength produced by a variable-wavelength laser.

An ocular for a set of safety goggles in accordance with the present invention can provide eye protection over the full operating wavelength band of a laser that produces radiation at selectable wavelengths within the wavelength band. A single-stage ocular according to the invention comprises, in combination, a dichroic sheet polarizer to establish a single polarization state for radiation from the laser, a wide-field birefringent element to create an optical path difference between orthogonal components of the polarization state of the radiation passed by the polarizer, and a quarter-wave tuning element to select the particular wavelength whose intensity is to be attenuated. Alternatively, in accordance with the present invention, each ocular of the set of safety goggles could comprise two or more stages used in tandem to attenuate radiation from extremely intense sources.

Two oculars according to the present invention would ordinarily be used as a coupled pair of eyepieces in a set of safety goggles, so that both eyes of the wearer of the goggles can be protected simultaneously. Matched tuning for the two oculars can be provided by a conventional gear train mechanism.

DESCRIPTION OF THE DRAWING

FIG. 1 is a schematic illustration in exploded view of the components of a tunable birefringent optical filter for use as a single-stage ocular in a set of safety goggles according to the present invention.

FIG. 2 is a perspective view of a set of safety goggles comprising a coupled pair of single-stage oculars as shown in FIG. 1.

FIG. 3 is a cross-sectional view of a single-stage ocular in the set of safety goggles as viewed along line 3—3 of FIG. 2.

FIG. 4 is a perspective view of a set of safety goggles comprising a coupled pair of double-stage oculars according to the present invention.

FIG. 5 is a plan view, partially broken away to show a cross section along line 5—5 of FIG. 4, of a portion of the set of safety goggles shown in FIG. 4.

BEST MODE OF CARRYING OUT THE INVENTION

FIG. 1 schematically illustrates the components of a tunable birefringent optical filter in exploded view. In accordance with drawing convention for schematically illustrating an optical system, light from a radiation source is considered to propagate from left to right through successively disposed components of the system. Thus, radiation from, e.g., a variable-wavelength laser entering the filter illustrated in FIG. 1 impinges upon a glass plate 10, which functions as a dust cover. The glass plate 10 passes substantially all the radiation impinging thereon to a polarizer 11, which establishes a single polarization state having a pass direction (as indicted on the polarizer 11 by a solid line) perpendicular to the direction of propagation of the radiation. The polarizer 11 could be, e.g., a thin dichroic sheet polarizer marketed by Polaroid Corporation of Cambridge, Mass. under catalog No. HN38.

The radiation as passed by the polarizer 11 with a single polarization state then enters a wide-field element comprising a uniaxial multiwave plate 12, a half-wave plate 13 and a uniaxial multiwave plate 14. The wide-field element introduces an optical path difference (i.e., a retardation) between orthogonal components of the radiation passed by the polarizer 11. The multiwave plates 12 and 14, each of which produces a retardation of a whole number (greater than 1) of waves, are made of a uniaxial crystal such as quartz, and are substantially identical to each other in configuration. The half-wave plate 13 prevents the individual retardations produced by the multiwave plates 12 and 14 from cancelling each other.

The multiwave plates 12 and 14 are disposed so that their optic axes are orthogonal to each other and are oriented at +45° and −45°, respectively, relative to the pass direction of the polarizer 11. The half-wave plate 13, which could be made of polyvinyl alcohol (PVA), is sandwiched between the multiwave plates 12 and 14 so that its optic axis is oriented parallel to the pass direction of the polarizer 11. The optic axes of the multiwave plates 12 and 14, and the optic axis of the half-wave plate 13, are indicated in FIG. 1 by broken lines on the respective components perpendicular to the direction of propagation of the radiation.

The output of the wide-field element passes to a tuning element, which can be adjusted to attenuate the intensity of radiation at a selected wavelength. The tuning element comprises a quarter-wave plate 15 that is stationary with respect to the components 12, 13 and 14 of the wide-field element, and a polarizing device that is rotatable with respect to the components 12, 13 and 14 of the wide-field element. The quarter-wave plate 15 transforms the output of the wide-field element, which is elliptically polarized with an ellipticity that is a function of wavelength, into a linear polarized wave whose orientation is a function of wavelength.

The quarter-wave plate 15 is sandwiched between the multiwave plate 14 of the wide-field element and a glass plate 16, which serves as a dust cover. The rotatable polarizing device, which comprises a glass plate 17, a thin dichroic polarizer 18 and a glass plate 19, permits selection of a particular wavelength for transmission through the filter. The polarizer 18 is sandwiched between the glass plates 17 and 19, which function as dust covers. There is a clearance between the stationary glass plate 16 and the rotatable glass plate 17 to permit relative rotation therebetween.

In a practical embodiment of the present invention as illustrated in FIG. 2, two tunable birefringent filters of the kind shown in FIG. 1 are mounted as a coupled pair of oculars in a set of safety goggles 20. For the birefringent filter comprising each ocular, the polarizer 11, the components of the wide-field element (i.e., the multiwave plate 12, the half-wave plate 13 and the multiwave plate 14), and the quarter-wave plate 15 are housed in a first (or "inner") cylindrical casing 21 in which the glass plates 10 and 16 are fitted as dust covers, and the polarizer 18 is housed in a second (or "outer") cylindrical casing 22 in which the glass plates 17 and 19 are fitted as dust covers.

It is immaterial which of the polarizers 11 and 18 functions as the entrance polarizer, and which functions as the exit polarizer, for each birefringent filter. Each filter produces the same result regardless of whether radiation is propagated through the ocular in a direction from the polarizer 11 through the components 12, 13 and 14 of the wide-field element and thence through the quarter-wave plate 15 to the polarizer 18, or in the opposite direction. In the embodiment of the invention shown in FIG. 2, the polarizer 18 (which is remote from the wearer's eye) functions as the entrance polarizer, and the polarizer 11 (which is positioned close to the wearer's eye) functions as the exit polarizer.

An arrangement is shown in cross-sectional detail in FIG. 3 for the mounting of each of the two coupled oculars in the set of safety goggles 20 illustrated in FIG. 2. For each ocular, the inner cylindrical casing 21 (housing the polarizer 11, the components 12, 13 and 14 of the wide-field element, and the quarter-wave plate 15) is fixedly secured in a correspondingly dimensioned aperture in an opaque front plate 23 of the set of goggles 20, so that the glass plate 10 can be positioned adjacent a corresponding one of the eyes of a wearer of the set of goggles 20. The outer cylindrical casing 22 (housing the polarizer 18) is mounted coaxially on the inner cylindrical casing 21 for relative rotation with respect thereto. The front plate 23 is attached in a conventional manner (as indicated in FIG. 2) to a flexible opaque frame 24, which is configured to conform to the upper front part of the head of the wearer over the wearer's eyes. A strap 25 is attachable in a conventional manner to the frame 24 to secure the set of goggles 20 to the wearer's head.

As shown in FIG. 3, an inwardly flanged end portion 26 of the inner cylindrical casing 21 provides a lip against which a circumferential edge portion of the glass plate 10 abuts. The optical components 11, 12, 13, 14 and 15 are disposed between the glass plate 10 and the glass plate 16 in sequential disposition along a common axis of the ocular. A snap ring 27, which may be made of metal, is positioned in an annular slot on the interior surface of the inner cylindrical casing 21 in such a way that an inner peripheral portion of the snap ring 27 extends radially inward to overlap a circumferential edge portion of the glass plate 16. The glass plates 10 and 16, and the components 11, 12, 13, 14 and 15 sandwiched therebetween, are thereby fixedly secured within the inner cylindrical casing 21.

An outwardly flanged elongate portion 28 of the inner cylindrical casing 21 provides a lip that abuts against a peripheral portion on one side of the front plate 23 circumjacent the correspondingly dimensioned aperture in which the inner cylindrical casing 21 is secured. A snap ring 29 is positioned in an annular slot on the exterior surface of the inner cylindrical casing 21 in such a way that an outer peripheral portion of the snap ring 29 extends radially outward to overlap a peripheral portion on the other side of the front plate 23 circumjacent the aperture in which the inner cylindrical casing 21 is secured. The inner cylindrical casing 21 is thereby firmly mounted in and maintained in stationary disposition with respect to the front plate 23.

The outer cylindrical casing 22 for each ocular is coaxially mounted on the inner cylindrical casing 21 for rotational movement with respect thereto. An inwardly flanged middle portion 30 of the outer cylindrical casing 22 provides a lip against which a circumferential edge portion of the glass plate 17 abuts. The polarizer 18 and the glass plate 19 are disposed in succession within the outer cylindrical casing 22 after the glass plate 17. A snap ring 31 is positioned in an annular slot on the interior surface of the outer cylindrical casing 22 in such a way that an inner peripheral portion of the snap ring 31 extends radially inward to overlap a circumferential edge portion of the glass plate 19. The glass plates 17 and 19, and the polarizer 18 sandwiched therebetween, are thereby fixedly secured within the outer cylindrical casing 22.

A longitudinally extending portion 32 of the outer cylindrical casing 22 overlaps the outwardly flanged elongate portion 28 of the inner cylindrical casing 21 to accomplish the coaxial mounting of the rotatable outer cylindrical casing 22 on the stationary inner cylindrical casing 21. As illustrated in FIG. 3, the interior surface of the longitudinally extending portion 32 of the outer cylindrical casing 22 engages the exterior surface of the outwardly flanged elongate portion 28 of the inner cylindrical casing 21 in a screw-threaded interface. However, a screw-threaded engagement of the overlapping portions 28 and 31 of the cylindrical casings 21 and 22, respectively, as shown in FIG. 3, is not the only way in which relative rotational motion between the cylindrical casings 21 and 22 can be provided. For example, a frictional interface (instead of a screw-threaded interface) could be provided between overlapping portions of the cylindrical casings 21 and 22.

A range of relative rotational motion through 180° for the cylindrical casings 21 and 22 is sufficient to permit selection of any wavelength in the bandpass of the birefringent filter comprising each ocular. In order to protect both eyes of the wearer, the outer cylindrical casings 22 of both oculars must be capable of simultaneous rotation through the same angle relative to the stationary inner cylindrical casings 21 so that both oculars can be tuned to the same wavelength. As illustrated in FIG. 2, the outer cylindrical casings 22 of the two oculars can be made to undergo the same angular rotation simultaneously by providing a dentate annular surface 33 on an exterior portion of each cylindrical casing 22, and by providing a correspondingly dentate annular surface on an exterior portion of an idler wheel 34 that is secured to the front plate 23 for cogwheel engagement with the dentate surfaces 33 on the cylindrical casings 22.

The idler wheel 34 can be secured to the front plate 23 by conventional means, as by a shaft 35 inserted through an aperture in the front plate 23. Thus, when the wearer turns the outer cylindrical casing 22 of either one of the oculars through a given angle, the outer cylindrical casing 22 of the other one of the oculars is correspondingly turned through the same angle. A knurled annular surface 36 on another exterior portion of the outer cylindrical casing 22 of each ocular facilitates turning of either one of the outer cylindrical casings 22 for tuning of the two birefringement filters simultaneously.

In order to limit the angular rotation of the outer cylindrical casing 22 with respect to the inner cylindrical casing 21 for each ocular, an arcuate slot 37 (preferably of 180° span) is provided on the idler wheel 34 as shown in FIG. 2 to receive a pin 38 projecting outward from the front plate 23. As the outer cylindrical casing 22 on either ocular is rotated, the idler wheel 34 is driven through a corresponding angle to rotate the outer cylindrical casing 22 on the other ocular. The pin 38, which is stationary, prevents rotation of the idler wheel 34 beyond angular limits (preferably defining a full range of 180°) as determined by the arc length of the slot 37.

For applications in which greater protection against intense optical radiation is required, two or more birefringent filter modules may be mounted in tandem as successive stages in a multi-stage ocular. It is only necessary that one rotatable polarizer 18 be used in conjunction with the stationary components of each two succesive stages in a multi-stage ocular. A set of safety goggles 20' comprising a pair of double-stage oculars is shown in perspective view in FIG. 4.

As illustrated in broken-away plan view in FIG. 5, the stationary components of the first stage of each double-stage ocular in the set of safety goggles 20' include the polarizer 11, the multiwave plate 12, the half-wave plate 13, the multiwave plate 14 and the quarter-wave plate 15, all of which are sandwiched between the glass dust cover plates 10 and 16. The stationary components of the second stage of each double-stage ocular comprise a glass dust cover plate 10', a polarizer 11', a multiwave plate 12', a half-wave plate 13', a multiwave plate 14', a quarter-wave plate 15', and a glass dust cover plate 16'. However, the stationary components of the second stage of the double-stage ocular are disposed in inverted sequence with respect to the disposition of the stationary components of the first stage along the direction of propagation of radiation through the ocular. The stationary components of the first and second stages are fixedly secured within an inner cylindrical casing 21', and the rotatable polarizer 18 (which is sandwiched between the glass dust cover plates 17 and 19) is disposed within the inner cylindrical casing 21' for rotation relative to the stationary components of the first and second stages.

An inwardly flanged end portion 26' of the inner cylindrical casing 21' provides a lip against which a circumferential edge portion of the glass plate 10 abuts. The optical components 11, 12, 13, 14 and 15 are disposed in succession between the glass plate 10 and the glass plate 16. A metal snap ring 27' is positioned in an annular slot on the interior surface of the inner cylindrical casing 21' in such a way that an inner peripheral portion of the snap ring 27' extends radially inward to overlap a circumferential edge portion of the glass plate 16.

As shown in FIG. 5, a retaining ring 39 made of a plastic material having a relatively low coefficient of friction, e.g., polytetrafluoroethylene (Teflon), is inserted into the interior of the inner cylindrical casing 21' so as to abut the snap ring 27'. The side of the retaining ring 39 abutting the snap ring 27' has an inwardly flanged end portion that provides a lip against which a circumferential edge portion of the glass dust cover plate 17 abuts. The polarizer 18 is disposed adjacent the glass plate 17, and the glass plate 19 is disposed after the polarizer 18. A snap ring 40 is positioned in an annular slot on the interior surface of the retaining ring 39 in such a way that an inner peripheral portion of the snap ring 40 extends radially inward to overlap a circumferential edge portion of the glass plate 19. The snap ring 40 thereby fixedly secures the components 17, 18 and 19 to the retaining ring 39.

Spaced axially apart from the snap ring 27', another metal snap ring 41 is position in another annular slot on the interior surface of the inner cylindrical casing 21' in such a way that an inner peripheral portion of the snap ring 41 extends radially inward to overlap a circumferential edge portion of the retaining ring 39. The snap rings 27' and 41 provide sides for an annular track on the interior surface of the inner cylindrical casing 21' within which the polarizer 18 can be made to undergo rotational motion with respect to the stationary components of the first and second stages of the ocular.

The glass dust cover plate 16' is disposed within the inner cylindrical casing 21' adjacent the snap ring 41, and the optical components 15', 14', 13', 12' and 11' are disposed in succession after the glass plate 16'. The glass dust cover plate 10' is disposed after the polarizer 11'. Spaced axially apart from the snap ring 41, another metal snap ring 42 is positioned in an annular slot on the interior surface of the inner cylindrical casing 21' in such a way that an inner peripheral portion of the snap ring 42 extends radially inward to overlap a circumferential edge portion of the glass plate 10'. The snap rings 27', 41 and 42 thereby fixedly secure the stationary components of the first and second stages of the ocular within the inner cylindrical casing 21'.

Rotation of the polarizer 18 with respect to the stationary components of the first and second stages of each multi-stage ocular of the set of goggles 20' is accomplished by providing a slot 43 of semi-annular (i.e., 180°) span in the inner cylindrical casing 21', and by securing the retaining ring 39 to an outer cylindrical casing 22' by means of a fastening pin 44 that passes through the slot 43. The outer cylindrical casing 22' fits coaxially over the inner cylindrical casing 21', and is rotatable with respect thereto. The angular limits on the rotation of the outer casing 22' with respect to the inner casing 21' are determined by the length of the slot 43. The fastening pin 44, which passes through an aperture in the outer casing 22' for screw-threaded penetration into the retaining ring 39, precludes rotation of the outer casing 22' and the attached retaining ring 39 beyond the ends of the slot 43.

The dentate annular surfaces 33 on the outer cylindrical casings 22' of the two oculars mesh with the correspondingly dentate annular surface on the idler wheel 34 secured to the front plate 23. Rotation of the outer cylindrical casing 22' on either one of the oculars through a given angle thereby causes the outer cylindrical casing 22' on the other one of the oculars to be turned through the same angle so that both oculars are simultaneously tuned to the same wavelength. The knurled annular surfaces 36 on the outer cylindrical casings 22' of the two oculars facilitate the turning of either one of the outer cylindrical casing 22' by the wearer of the set of goggles 20'.

Single-stage oculars as illustrated in FIGS. 2 and 3 would generally produce an attenuation in intensity by a factor of about $10^3$, and would therefore provide adequate eye protection for most CW and low-power laser applications. Multi-stage oculars can provide, depending upon the number of stages, correspondingly greater attenuation. A three-stage ocular could provide attenuation by a factor on the order of $10^9$.

Particular embodiments of eye-protective safety goggles in accordance with the present have been described herein. However, other embodiments suitable for particular applications would become apparent to workers skilled in the art upon perusal of the foregoing specification and accompanying drawing. The description presented herein is to be understood as illustrative of the invention, which is more generally defined by the following claims and their equivalents.

I claim:

1. Eye-protective goggles for attenuating optical radiation produced by a variable-wavelength radiation source, said goggles comprising a pair of oculars, each of said oculars including a birefringent filter that is tunable to a selected wavelength producible by said radiation source, both of said oculars being coupled so that the birefrigent filters in both of said oculars are simultaneously tunable to said selected wavelength.

2. The eye-protective goggles of claim 1 wherein said birefringent filter in each ocular comprises in sequential disposition along a common axis of said ocular:
    (a) a first polarizer,
    (b) a first uniaxial multiwave plate for producing a retardation of more than one wave,
    (c) a half-wave plate,
    (d) a second uniaxial multiwave plate for producing a retardation of more than one wave,
    (e) a quarter-wave plate, and
    (f) a second polarizer;
said goggles further comprising means for positioning each of said oculars adjacent a corresponding one of a wearer's eyes, and means for rotating said second polarizer through an angle relative to said first polarizer for each of said oculars.

3. The eye-protective goggles of claim 2 wherein said first polarizer, said first multiwave plate, said half-wave plate, said second multiwave plate and said quarter-wave plate of each of said oculars are fixedly mounted in sequential disposition between a first transparent plate and a second transparent plate within a first generally cylindrical casing; wherein said second polarizer of each of said oculars is fixedly mounted between a third transparent plate and a fourth transparent plate within a second generally cylindrical casing; and wherein said second casing is mounted coaxially on said first casing for rotational motion with respect to said first casing.

4. The eye-protective goggles of claim 3 wherein a dentate portion of said second casing of each of said oculars meshes with a correspondingly dentate portion of an idler wheel so that rotation of the second casing of one of said oculars through a selected angle causes simultaneous rotation of the second casing of the other of said oculars through substantially the same selected angle.

5. The eye-protective goggles of claim 1 wherein each ocular comprises a plurality of biregrigent filter stages positioned in tandem along a common axis of said ocular, each birefrigent filter stage including as stationary components:
    (a) a first polarizer,
    (b) a first uniaxial multiwave plate for producing a retardation of more than one wave,
    (c) a half-wave plate,
    (d) a second uniaxial multiwave plate for producing a retardation of more than one wave, and
    (e) a quarter-wave plate;
the stationary components of a first one of sid filter stages being disposed in inverse sequential order with respect to the stationary components of a second one of said filter stages, a rotatable polarizer being interposed between said first and second ones of said filter stages, said rotatable polarizer functioning as a polarizing component for each of said first and second ones of said filter stages.

6. The eye-protective goggles of claim 5 wherein said first and second ones of said filter stages are fixedly mounted spaced apart from each other within a first generally cylindrical casing, and wherein said rotatable polarizer is positioned coaxially within said first casing between said first and second ones of said filter stages, said first casing having an elongately apertured portion, said rotatable polarizer being connected through said elongately apertured portion of said first casing to a second generally cylindrical casing, said second casing being coaxially mounted on said first casing for relative rotation with respect to said first casing, rotation of said second casing with respect to said first casing causing corresponding rotation of said rotatable polarizer with respect to the stationary components of said first and second ones of said filter stages.

7. The eye-protective goggles of claim 6 wherein the first polarizer of the first one of said filter stages is positioned adjacent a first transparent plate, the quarter-wave plate of said first one of said filter stages is positioned adjacent a second transparent plate, the first polarizer of the second one of said filter stages is positioned adjacent a third transparent plate, and the quarter-wave plate of the second one of said filter stages is positioned adjacent a fourth transparent plate; and wherein said rotatable polarizer is sandwiched between a fifth transparent plate and a sixth transparent plate, said fifth transparent plate facing said second transparent plate across a gap separating the stationary components of said first one of said filter stages from said rotatable polarizer, said sixth transparent plate facing said fourth transparent plate across a gap separating the stationary components of said second one of said filter stages from said rotatable polarizer.

8. The eye-protective goggles of claim 7 further comprising means for positioning each of said oculars adjacent a corresponding one of the eyes of a wearer, and means for rotating said rotatable polarizer through an angle relative to the first polarizers of said first and second ones of said filter stages simultaneously for each of said oculars.

9. The eye-protective goggles of claim 8 wherein a dentate portion of the second casing of each of said oculars engages a correspondingly dentate portion of an idler wheel so that rotation of the second casing of one of said oculars through a selected angle causes simultaneous rotation of the second casing of the other of said oculars through substantially the same selected angle.

* * * * *